(12) United States Patent
Sander

(10) Patent No.: US 6,312,730 B1
(45) Date of Patent: Nov. 6, 2001

(54) PSYLLIUM-HYDROCOLLOID GUM COMPOSITION

(75) Inventor: Eugene H. Sander, Hayfield, MN (US)

(73) Assignee: Johnson & Johnson. Merck Consumer Pharmaceuticals, Co., New Brunswick, NJ (US)

( * ) Notice: Subject to any disclaimer, the term of this patent is extended or adjusted under 35 U.S.C. 154(b) by 0 days.

(21) Appl. No.: 08/329,726

(22) Filed: Oct. 26, 1994

Related U.S. Application Data

(63) Continuation of application No. 07/911,428, filed on Jul. 10, 1992, now abandoned.

(51) Int. Cl.[7] ............................... A61K 9/14; A61K 9/16; A61K 35/78
(52) U.S. Cl. ...................... 424/496; 424/489; 424/490; 424/738; 514/782; 514/892; 514/911
(58) Field of Search ................................ 424/195.1, 493, 424/496, 439, 489, 490, 738, 725; 514/782, 892, 974, 911

(56) References Cited

U.S. PATENT DOCUMENTS

| | | | |
|---|---|---|---|
| 1,891,698 | * 12/1932 | Tuvin | 424/496 |
| 4,851,392 | * 7/1989 | Shaw et al. | 514/53 |
| 5,149,541 | * 9/1992 | Leis, Jr. et al. | 424/489 |

* cited by examiner

*Primary Examiner*—James M. Spear
(74) *Attorney, Agent, or Firm*—Woodcock Washburn Kurtz Mackiewicz & Norris LLP

(57) ABSTRACT

A rapidly dispersible powder having use as a laxative and fiber supplement, comprising psyllium particles coated with gum arabic. The present invention also includes a method for making the powder that includes providing an effective quantity of gum arabic to a fluidized bed having the psyllium particles to make the rapidly dispersible powder. The present invention further includes a method for making a constipation treatment and a treatment for fiber supplementation.

12 Claims, No Drawings

PSYLLIUM-HYDROCOLLOID GUM COMPOSITION

This is a continuation, of application Ser. No. 07/911,428, filed Jul. 10. 1992, now abandoned.

BACKGROUND OF THE INVENTION

The present invention relates to a powder that comprises psyllium particles coated with gum arabic.

Psyllium seed husk has use as a fiber supplement and a bulk laxative drug because the psyllium seed husk has a capacity for substantial swelling when ingested. This swelling makes the psyllium husk a useful bulking agent. Ingestion of psyllium seed husk has been demonstrated to yield a number of benefits to the consumer, including Taxation, appetite suppression and cholesterol reduction.

The psyllium seed includes a husk portion that is a cleaned, dried seed coat of the psyllium seed. The husk portion is separated from the seed by winnowing and thrashing. Typically, the husk portion of the psyllium seed is ground into a powder to make the bulk laxative drug. The psyllium bulk laxative drug powder is then ingested by a consumer after the consumer stirs the powder into a glass of water.

The use of the psyllium husk powder as a bulk laxative has not been universally accepted by consumers, however, because the powder does not readily disperse in water. In particular, the psyllium husk powder does not disperse in water with simple stirring. Instead, the psyllium husk powder aggregates to form gel-coated lumps. The gel-coated lumps have interiors that are substantially dry. Additionally, the gel-coated lumps tend to float on the surface of water causing the lumps to clump into large masses.

Attempts have been made to improve the dispersibility of psyllium husk powder in water. The attempts have included controlling particle size of the psyllium powder during a processing step of size reduction. The Meer et al. patent, U.S. Pat. No. 4,996,051, issued Feb. 26, 1991, describes a product that includes apple fiber, fructose, gum arabic, flavors and psyllium husk powder having a particle size that passes through a No. 50 mesh screen.

The attempts have also included coating the particles of psyllium powder with a surface coating. One surface coating described by Colliopoulos et al. in U.S. Pat. No. 4,459,280, includes a dispersing agent, maltodextrin. A second surface coating described by Powell et al. U.S. Pat. No. 4,321,263, includes one of the dispersing agents, propylene glycol (PG) or polyvinyl pyrrolidone (PVP) or a blend of PG and PVP. The use of PVP and PG is, however, limited by handling problems resulting from high viscosities developed in PVP and PG solutions.

The PG or PVP dispersing agents are applied to psyllium particles with non-aqueous solvent carriers such as volatile alcohol. The use of volatile alcohol to deliver PG, PVP or blends of PG and PVP to psyllium powder surfaces during processing has presented safety problems to many processors because the alcohol is flammable.

A third attempt to improve psyllium husk powder dispersibility has included cold blending. Cold blending includes mixing psyllium powder with granular diluents such as sucrose and dextrose. Other granular diluents include chemical compounds capable of reacting when in contact with moisture to produce carbon dioxide. The granular diluents are added in concentrations of up to 50% of the cold blend.

The cold blending of psyllium with granular diluents has created a situation where the more dense diluent will fall to the bottom of a glass of water while the psyllium powder will ball up near or on the surface of the water. Moreover, the solubility of the granular diluents is much higher than the psyllium husk powder. This increased solubility favors rapid dispersibility, and more importantly, dissolution of the granular diluents. However, the psyllium powder is left behind in an undispersed state.

One other problem of cold blending psyllium powder with a granular diluent such as sucrose or dextrose is that these diluents are metabolizable sugars. As such, their use by consumers in a psyllium bulk laxative is limited to non-diabetic consumers.

One other attempt to improve psyllium dispersibility has included preparing a tablet having a psyllium powder component. The Casillan patent, U.S. Pat. No. 4,999,200, describes a tablet that includes psyllium powder, a gelling agent such as polysorbate 80, a binding agent such as polyvinyl pyrollidone or acacia and a disintegrant such as microcrystalline cellulose. The tablet disintegrates in the gastrointestinal tract of a consumer.

Another attempt to improve psyllium powder dispersibility has included coextrusion of psyllium husks with citric acid under controlled heating conditions. The coextrusion is believed to effect a reduction in microbial growth and to improve dispersibility.

SUMMARY OF THE INVENTION

The present invention includes a rapidly dispersible powder having use as a laxative and a fiber supplement, a method for making the powder and a method for preparing a treatment for constipation and fiber supplementation.

The powder includes psyllium particles coated with gum arabic. The powder, having use as a bulk laxative and fiber supplement, disperses rapidly in dispersing media such as water.

The method for making the rapidly dispersible powder includes fluidizing the psyllium particles and applying to the fluidized particles, an aqueous solution that includes gum arabic. The gum arabic solution is applied to the fluidized particles in a manner that promotes a uniform distribution of the gum arabic solution over the psyllium particles. The gum arabic solution is also applied in a manner that produces a powder having a particle size distribution, moisture and bulk density that improve dispersibility of psyllium in water.

The method for treating constipation and providing fiber supplementation includes providing an effective quantity of the rapidly dispersible powder. The method also includes providing an effective quantity of dispersing media such as water and rapidly dispersing the powder into the dispersing media.

DETAILED DESCRIPTION OF THE PREFERRED EMBODIMENTS

The present invention includes a rapidly dispersible powder having use as a laxative and a fiber supplement, that includes psyllium particles coated with gum arabic. The present invention also includes a method for making the powder and a method for preparing a constipation treatment and a fiber supplement using the powder.

The psyllium-gum arabic particles preferably include a gum arabic content of at least about 5% by weight. Most preferably, the gum arabic content is about 5% by weight. The powder also includes a moisture concentration within a range of about 2.8 to 6.6% by weight. The powder may optionally include flavorants and a sweetener such as aspartame. The remaining powder weight is substantially psyllium.

The rapidly dispersible powder of the present invention includes a bulk density within a range of about 0.394 to about 0.609. The powder has an approximate particle size distribution range as described in Table 1.

TABLE 1

Particle Size Distribution

| U.S. Standard Sieve Screen | Percent Retained on Screen |
| --- | --- |
| 10 mesh | 0.0 |
| 40 mesh | 0.0–2.4 |
| 60 mesh | 2.4–28 |
| 100 mesh | 30.6–55 |
| 140 mesh | 16.4–36.0 |
| 200 mesh | 3.6–16.0 |
| PAN | 0.6–9.0 |

The rapidly dispersible powder does not form lumps when stirred into water with a spoon for ten seconds. In one dispersibility test, five grams of the powder was stirred into 227 milliliters of water with a spoon. The powder particles did not clump together or aggregate at the top of the glass. The powder was substantially dispersed in the water.

The psyllium component of the powder is derived from the husk of the psyllium seeds. Psyllium seeds, also called plantago seeds and flea seeds, are acceptably obtained from the plants *Plantago ovata, Plantago psyllium L.* or *P. Arenaria. Plantago ovata* is the major commercial source of psyllium. The psyllium seeds are small, dark, reddish brown, odorless, and almost tasteless seeds.

The husk is separated from the psyllium seed and is ground into particles. In one preferred psyllium husk particle embodiment, illustrated in Table 2, the psyllium husk particles included a moisture of about 9% by weight and a bulk density of about 0.617. The psyllium husk particles also included a particle size distribution that is described in Table 2.

TABLE 2

| PARAMETER | VALUE |
| --- | --- |
| Moisture | 9.0% |
| Bulk Density | 0.617 g/cc |
| Particle Size Distribution | |
| 100 mesh | 35.6 retained on screen |
| 140 mesh | 37.2 retained on screen |
| 200 mesh | 14.8 retained on screen |
| Pan | 11.6 retained on screen |

Most preferably, the husk includes a hydrating psyllium husk.

The gum arabic component of the powder, also called Acacia, is derived from the dried gummy exudation of the stems and branches of *Acacia senegal,* Leguminosae or other African species of Acacia. The gum arabic component is a low viscosity hydrocolloid gum. Gum arabic is most preferred for use in the present invention because solutions of gum arabic having concentrations of gum arabic of up to about 30% by weight are convenient to make. Also, gum arabic is a good film former and by itself is a natural, soluble fiber. Other desirable features of gum arabic as a component of the present invention includes the easy dispersion of gum arabic in cold water. Also, gum arabic can be used at high concentrations without generating excess solution viscosity. Excessive solution viscosity limits the capacity of a gum to be physically pumped and atomized into a fluidized bed.

The gum arabic component of the rapidly dispersing powder also increases the viscosity of the dispersing media such as water, enough to hold the powder in suspension. Consequently, the powder does not settle into a visible layer and does not require further stirring in order to suspend the layer before consuming. As a result, the powder does not form small fish eyes that create a negative palatability when consumed.

The method of making the rapidly dispersible powder includes providing an effective quantity of psyllium husk particles to a fluidized bed, fluidizing the psyllium husk particles, providing an effective quantity of gum arabic to make an aqueous gum arabic solution, and spraying the gum arabic solution onto the fluidized psyllium husk particles to make particles that are coated with gum arabic. The powder of the present invention includes individual psyllium husk particles coated with gum arabic. The powder of the present invention also includes agglomerated psyllium husk particles coated with gum arabic.

In one preferred embodiment, the psyllium husk particles were placed in a bowl of a Glatt WSG fluidizing dryer such as is made by Glatt Air Techniques of Ramsey, N.J. The Glatt WSG had a capacity of 5 kilograms. Although a batch-type fluidized bed dryer system is specifically referred to, any system that coats or agglomerates psyllium husk particles with a gum arabic solution is included within the present invention.

The fluidized bed dryer includes an entry through which heated air is introduced and distributed so that the psyllium husk particles are fluidized. The fluidized psyllium husk particles are then sprayed with a liquid solution of water and gum arabic from an atomizing spray nozzle located above the fluidizing bed. In one other embodiment, a plurality of atomizing spray nozzles are arranged concentrically about and around the fluidizing bed. The psyllium particles, as they move through the fluid bed, are alternately sprayed and dried, with a residence time of each spraying interval lasting long enough to wet the surface of the particles.

Although the exact mechanism of agglomeration is not known, the following explanation is believed to be true. In the fluidized bed, the psyllium particles are moving about, colliding with each other. During spraying, the surfaces of the particles become wet and tacky with the gum arabic solution, resulting in the particles sticking to each other after a collision. When the particles move away from the spray nozzle, the air dries the particles and the particles become bound to each other. Spraying and drying intervals are continued until agglomerated particles are formed.

Preferably, the agglomerated particles are allowed to build so that the particle size distribution is such that about 80% will pass through a 60 mesh screen but will be retained on a 140 mesh screen. The particles are also agglomerated so that the gum arabic solution will coat the outside of the agglomerated particles to form the rapidly dispersible powder. The gum arabic content of the agglomerated particles is preferably at least about 5% by weight. Most preferably, the gum arabic component is about 5% of the agglomerated particles by weight.

The method of preparing a treatment for constipation and fiber supplementation includes providing a dosage of the rapidly dispersible powder of the present invention. Most preferably, the dosage includes about 3 to 4 grams of the powder. The method also includes providing an effective quantity of dispersing media. The most preferred dispersing media is water. Most preferably, the effective quantity of water includes about one cup. The method further includes combining the dosage of the powder with the water to form a mixture and stirring the mixture to rapidly disperse the powder.

The following are examples of the process and product of the present invention. The examples are not intended to limit the invention but are intended to more fully describe the present invention.

EXAMPLE 1

A quantity of 3800 grams of psyllium husk particles having physical characteristics described in Table 2 was placed in the bowl of a Glatt WSG 5 fluid bed dryer manufactured by Glatt Air Techniques, Ramsey, N.J. Separately, a 27% aqueous solution of gum arabic was prepared and was delivered to the fluid bed dryer by means of a peristaltic pump. The gum arabic was spray gum C, obtained from Colloids Naturals, Inc., Bridgewater, N.J. The gum arabic solution was pumped at a rate which insured optimum operating conditions in the fluid bed dryer. The gum arabic solution was also pumped in an amount which insured a content of about 5% gum arabic in the psyllium-gum arabic powder. The amount pumped was about 200 gms of gum arabic.

For the run, a two-fluid nozzle was used to deliver the gum arabic solution. The nozzle height was set at No. 0.5. The port size was 1.8 mm. The angle setting was 2.5 turns. The spray interval was 30 seconds. The atomizing air pressure was 3.0 bar. The shake interval was 5 seconds. The air used to fluidize the particles had an inlet temperature of 102 degrees C. The exhaustion damper setting was 0.75% open. The final product sifter used was 20 mesh.

The psyllium—gum arabic powder produced had a moisture level of about 4.8%. The bulk density was about 0.609. The particle size distribution of powder particles is described as follows:

| Mesh Size | Percent Retained |
| --- | --- |
| 10 | 0.0 |
| 40 | 0.0 |
| 60 | 4.0 |
| 100 | 42.2 |
| 140 | 35.6 |
| 200 | 16.0 |
| PAN | 2.0 |

When 5 grams of the powder of the present invention were stirred into 227 mls of water, the powder did not form lumps in the water.

EXAMPLE 2

A quantity of 340.5 kilograms of psyllium husk particles was placed in the processing bowl of a Glatt WSG Model 300 fluid bed dryer. The psyllium husk particles were Psyberloid SR 4822 made by Botanicals International and obtained from Long Beach, Calif. The psyllium husk particles had the physical characteristics described in Table 2. Similarly to Example 1, an aqueous gum arabic solution of 33% was prepared and was delivered to the fluid bed dryer under controlled conditions so that the final gum arabic content was about 5% in the finished powder.

The powder produced had a moisture of 2.8%. The bulk density of the powder was 0.59. The particle size distribution of the powder is described as follows:

| Mesh Size | Percent Retained |
| --- | --- |
| 10 | 0.0 |
| 40 | 0.4 |
| 60 | 6.2 |
| 100 | 53.8 |
| 140 | 29.4 |
| 200 | 7.8 |
| PAN | 3.4 |

The powder did not form lumps when 5 gms were stirred into 227 mls of water with a spoon for 10 seconds.

EXAMPLE 3

The process of Example 3 was performed as for Example 1 with one difference. The difference was that the gum arabic of the final product was increased to 10%. The process produced a powder having a moisture of 6.6%. The bulk density was 0.546. The particle size distribution of the powder was as follows:

| Mesh Size | Percent Retained |
| --- | --- |
| 10 | 0.0 |
| 40 | 2.4 |
| 60 | 18.6 |
| 100 | 54.8 |
| 140 | 19.6 |
| 200 | 4.0 |
| PAN | 0.6 |

EXAMPLE 4

The process was run according to the description of Example 1 with one change. The change was that dry gum arabic was co-blended with the dry psyllium husk particles in the fluid bed dryer bowl. The particles were sprayed with cold water, not a gum arabic solution.

The process produced a powder having a moisture of 6.2%. The bulk density was 0.501. The particle size distribution of the powder was as follows:

| Mesh Size | Percent Retained |
| --- | --- |
| 10 | 0.0 |
| 40 | 0.6 |
| 60 | 12.4 |
| 100 | 55.0 |
| 140 | 23.4 |
| 200 | 5.8 |

EXAMPLE 5

The process was performed as for Example 1 with these exceptions. The psyllium husk particles were partially agglomerated with cold water and then sprayed with a 27% aqueous gum arabic solution.

The powder produced by the process had a moisture of 6.3% and a bulk density of 0.511. The particle size distribution of the powder was as follows:

| Mesh Size | Percent Retained |
|---|---|
| 10 | 0.0 |
| 40 | 3.8 |
| 60 | 25.0 |
| 100 | 50.8 |
| 140 | 16.6 |
| 200 | 3.6 |
| PAN | 0.6 |

Although the present invention has been described with reference to preferred embodiments, workers skilled in the art will recognize that changes may be made in form and detail without departing from the spirit and scope of the invention.

What is claimed is:

1. A process for producing a bulk fiber composition consisting essentially of:
   a) preparing an aqueous solution of gum acacia;
   b) mixing powdered psyllium husks with said aqueous solution of gum acacia by fluidized bed agglomeration; and
   c) drying the mixture to form a dry, free-flowing, water dispersible, agglomerated dietary fiber combinate.

2. The process of claim 1 wherein the gum acacia is present in an amount of at least 5% by weight.

3. The process of claim 2 wherein the particles contain about 2.8 to 6.6 percent water and the remaining weight is substantially psyllium.

4. The process of claim 1 wherein a flavorant is added to the particles.

5. The process of claim 1 wherein a sweetener is added to the particles.

6. A consumable bulk fiber composition consisting essentially of powdered psyllium husks agglomerated with gum acacia, said gum acacia being present in an amount of at least 5 percent by weight of said composition, moisture being present within a range of about 2.8 to about 6.6 percent, with the remaining weight substantially psyllium.

7. The composition of claim 6 additionally containing a flavorant.

8. The composition of claim 6 additionally containing a sweetener.

9. A process for producing a bulk fiber composition consisting essentially of:
   a) preparing an aqueous solution of gum acacia,
   b) mixing powdered psyllium husks with said aqueous solution of gum acacia, and
   c) drying the mixture to form a dry, free-flowing water dispersible dietary fiber combinate, said gum acacia being present in an amount of at least 5 percent by weight of said composition, moisture being present within a range of about 2.8 to about 6.6 percent, with the remaining weight substantially psyllium.

10. A process for producing a bulk fiber composition consisting essentially of:
    a) preparing an aqueous solution of gum acacia;
    b) mixing powdered psyllium husks with said aqueous solution of gum acacia, said gum acacia being present in an amount to yield at least about 5 percent by weight of said composition after drying; and
    c) drying the mixture to form a dry, free-flowing, water dispersible, agglomerated dietary fiber combinate.

11. The method of claim 10 wherein said gum acacia is present in an amount to yield up to about 10 percent by weight of said composition after drying.

12. A consumable bulk fiber composition consisting essentially of powdered psyllium husks agglomerated with gum acacia, said gum acacia being present in an amount of from about 5 to about 10 percent by weight of the composition, moisture being present in an amount of from about 2.8 to about 6.6 percent by weight of the composition, with the remaining weight substantially psyllium in an amount of from about 83.4 to about 92.2 percent by weight of the composition.

* * * * *